United States Patent
Schulz et al.

(10) Patent No.: US 9,097,671 B2
(45) Date of Patent: Aug. 4, 2015

(54) ASSAYS

(71) Applicant: Clondiag GmbH, Jena (DE)

(72) Inventors: Torsten Schulz, Jena (DE); Thomas Kaiser, Hohlstedt (DE); Thomas Uhlig, Jena (DE); Klaus Peter Möbius, Zollnitz (DE); Alexander von Schenk zu Schweinsberg, Jena (DE)

(*) Notice: Subject to any disclaimer, the term of this patent is extended or adjusted under 35 U.S.C. 154(b) by 133 days.

(21) Appl. No.: 13/688,606

(22) Filed: Nov. 29, 2012

(65) Prior Publication Data

US 2014/0148365 A1 May 29, 2014

Related U.S. Application Data

(63) Continuation of application No. 12/516,070, filed as application No. PCT/EP2007/062716 on Nov. 22, 2007, now Pat. No. 8,349,616.

(60) Provisional application No. 60/867,019, filed on Nov. 22, 2006.

(51) Int. Cl.
    *G01N 21/75* (2006.01)
    *G01N 31/22* (2006.01)
    *G01N 21/64* (2006.01)
    *B01L 3/00* (2006.01)
    *G01N 33/52* (2006.01)

(52) U.S. Cl.
    CPC ........ *G01N 21/6454* (2013.01); *B01L 3/50273* (2013.01); *B01L 2300/0636* (2013.01); *B01L 2300/087* (2013.01); *B01L 2300/0816* (2013.01); *B01L 2300/0819* (2013.01); *B01L 2400/0481* (2013.01)

(58) Field of Classification Search
    CPC ............... G01N 27/3273; G01N 35/00069
    USPC ................................. 422/402, 404
    See application file for complete search history.

(56) References Cited

U.S. PATENT DOCUMENTS

| 5,255,074 A | * | 10/1993 | Kimbell et al. ............... 356/445 |
| 5,324,633 A | | 6/1994 | Fodor et al. |
| 6,838,680 B2 | | 1/2005 | Maher et al. |
| 2002/0037499 A1 | * | 3/2002 | Quake et al. ..................... 435/5 |

(Continued)

FOREIGN PATENT DOCUMENTS

| WO | WO 2005/108604 | 11/2005 |
| WO | WO 2007/051861 | 5/2007 |

*Primary Examiner* — Jill Warden
*Assistant Examiner* — Brittany Fisher
(74) *Attorney, Agent, or Firm* — Steptoe & Johnson LLP (57) ABSTRACT

A method for assaying a sample for each of multiple analytes is described. The method includes contacting an array of spaced-apart test zones with a liquid sample (e.g., whole blood). The test zones are disposed within a channel of a microfluidic device. The channel is defined by at least one flexible wall and a second wall which may or may not be flexible. Each test zone comprising a probe compound specific for a respective target analyte. The microfluidic device is compressed to reduce the thickness of the channel, which is the distance between the inner surfaces of the walls within the channel. The presence of each analyte is determined by optically detecting an interaction at each of multiple test zones for which the distance between the inner surfaces at the corresponding location is reduced. The interaction at each test zone is indicative of the presence in the sample of a target analyte.

14 Claims, 6 Drawing Sheets

(56) References Cited

U.S. PATENT DOCUMENTS

| | | |
|---|---|---|
| 2003/0038248 A1 | 2/2003 | Maher et al. |
| 2003/0108868 A1 | 6/2003 | Richards |
| 2004/0018523 A1 | 1/2004 | Hawkins |
| 2005/0036146 A1* | 2/2005 | Braig et al. .................. 356/436 |
| 2005/0037384 A1* | 2/2005 | Braig et al. ....................... 435/6 |
| 2005/0106749 A1* | 5/2005 | Braig et al. ................... 436/169 |
| 2006/0257286 A1* | 11/2006 | Adams ....................... 422/82.01 |
| 2011/0268626 A1* | 11/2011 | Slowey et al. ................ 422/402 |
| 2012/0115757 A1* | 5/2012 | Adams ........................... 506/39 |

\* cited by examiner

ASSAYS

PRIORITY CLAIM

This application claims priority to U.S. patent application Ser. No. 12/516,070, filed Jul. 14, 2009, which claims priority under 35 USC 371 to International Application No. PCT/EP2007/062716, filed Nov. 22, 2007, which claims priority to U.S. Provisional Application No. 60/867,019 filed on Nov. 22, 2006, each of which is incorporated herein by reference in its entirety.

FIELD OF THE INVENTION

The present invention relates to assays (e.g., assays for multiple analytes in a sample).

RELATED APPLICATIONS

This application is related to U.S. provisional application 60/826,678 filed 22 Sep. 2006 and to the U.S. continuation of International Patent Application PCT/EP2005/004923, filed 6 May 2005, which designates the United States and claims priority to German Patent Application DE 10 2004 022 263, filed 6 May 2004, the U.S. continuation having Ser. No. 11/593,021 and being filed 6 Nov. 2006. Each of the foregoing applications is incorporated herein by reference in its entirety.

BACKGROUND

Assays can be performed to determine the presence of one or more analytes in a sample. Arrays can be used to perform multiple assays (e.g., for each of multiple different analytes) on a sample. Typical arrays include a substrate having multiple spaced apart test zones each having a different probe compound such as a polynucleotide, antibody, or protein. In use, the array is contacted with a sample, which then interacts with the sites of the array. For each site, the interaction can include, for example, binding of a corresponding analyte to probe compounds of the site and/or a chemical reaction between the corresponding analyte and the probe compounds. The reaction results in a detectable product (e.g., a precipitate). The presence and extent of interaction depends upon whether a corresponding analyte is present in the sample. Typically, the interaction is detected optically (e.g., by fluorescence). For example, optical detection can be performed using an imaging detector (e.g., a CCD) having multiple light sensitive elements (e.g., pixels) spaced apart from one another in at least one (e.g., two) dimensions. Each of the light sensitive elements is positioned to receive light from a different spatial location of the substrate. Thus, light simultaneously detected by multiple light sensitive elements can be combined to form image data in at least one (e.g., two) dimensions of the substrate. The image data can be evaluated to determine the presence and/or extent of interaction at multiple sites of the array.

SUMMARY OF THE INVENTION

The present invention relates to assays (e.g., assays for multiple analytes in a sample).

BRIEF DESCRIPTION OF THE DRAWINGS

FIGS. 3b to 3g illustrate a method for forming the test zone of FIG. 3a.
FIGS. 4 and 5 are side views of a system configured to operate the microfluidic device of FIG. 1;
FIG. 5 is only a partial side view.

DETAILED DESCRIPTION OF THE INVENTION

A method for assaying a sample to determine the presence (e.g., qualitatively and/or quantitatively) of multiple analytes includes introducing the sample into a channel of a microfluidic device. The channel is defined between opposed inner surfaces of first and second substrates of the device. The second substrate is relatively flexible compared to the first substrate. Multiple test zones are spaced apart along the channel. Each test zone includes an immobilized probe compound configured to participate in an assay for a respective analyte. Typically, each assay includes interaction of the probe compound with the respective analyte or with a respective complex including the analyte and a reagent (e.g., an optical label).

To determine the assay result for each test zone, the outer surface of the second substrate is subjected to a localized compressive force. The compressive force causes a localized reduction of the distance separating the inner surfaces of the first and second substrates. The location of the localized distance reduction overlaps an optical detection zone defined within the channel. As the distance is reduced, mobile material (e.g., sample, unbound optical probes, and/or reagents) is displaced from between the substrates at the detection zone. The microfluidic device is translated so that the test zones pass sequentially through the detection zone. For each test zone, the assay result is optically determined (e.g., by fluorescence) as the test zone passes through the detection zone. The presence of each analyte is determined (e.g., quantitatively and/or qualitatively) based on the assay result.

The material displaced from the detection zone would otherwise contribute to background optical signals (e.g., background fluorescence). Accordingly, displacing such material can improve the signal-to-noise for the determination of the assay results. The assay results can typically determined without first contacting the test zones with a wash solution after contacting the test zones with the sample. The analytes to be determined can be selected as desired. For example, the analytes can relate to medicine (e.g., diagnostics), research (e.g., drug discovery), industry (e.g. water or food quality monitoring), or forensics. Exemplary analytes to be determined include markers (e.g., diagnostic markers or predictive markers) of physiological conditions such as disease. Such markers include cardiac markers (e.g., natriuretic peptides and members of the troponin family), cancer markers (e.g., nuclear matrix proteins), genetic markers (e.g., polynucleotides), sepsis markers, neurological markers, and markers indicative of pathogenic conditions. The analytes may be indicative of the presence of pathogens (e.g., bacteria, viruses, or fungi).

The probe compounds of the test zones can be selected as desired based on the analytes to be determined. Exemplary probe compounds include polynucleotides, antibodies, and proteins.

The sample liquid can be selected as desired based on the analytes to be determined. Exemplary samples include water, aqueous solutions, organic solutions, inorganic solutions, bodily fluids of humans and other animals, for example, urine, sputum, saliva, cerebrospinal fluid, whole blood and blood-derived materials such as plasma and sera.

Figure 1:
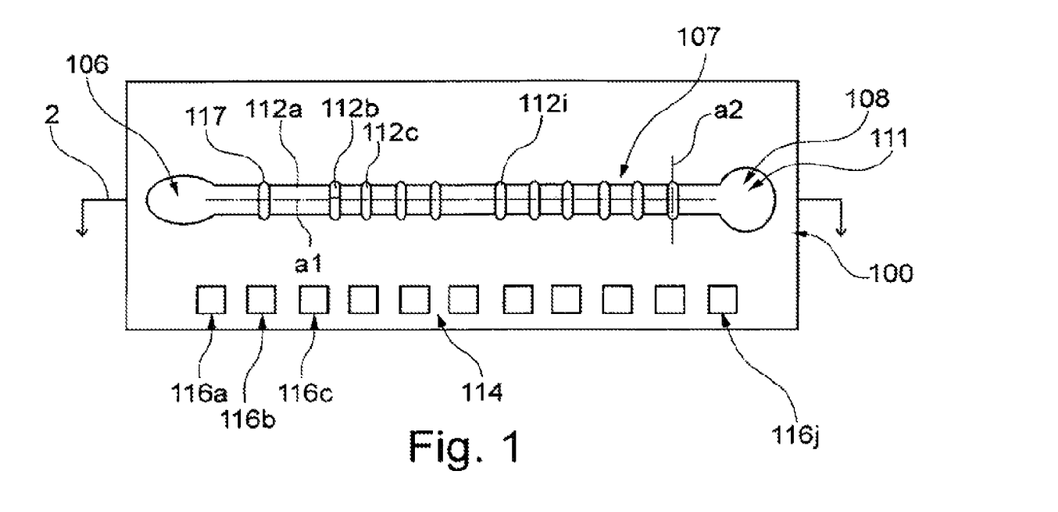
FIG. 1 is a microfluidic device.
Figure 2:
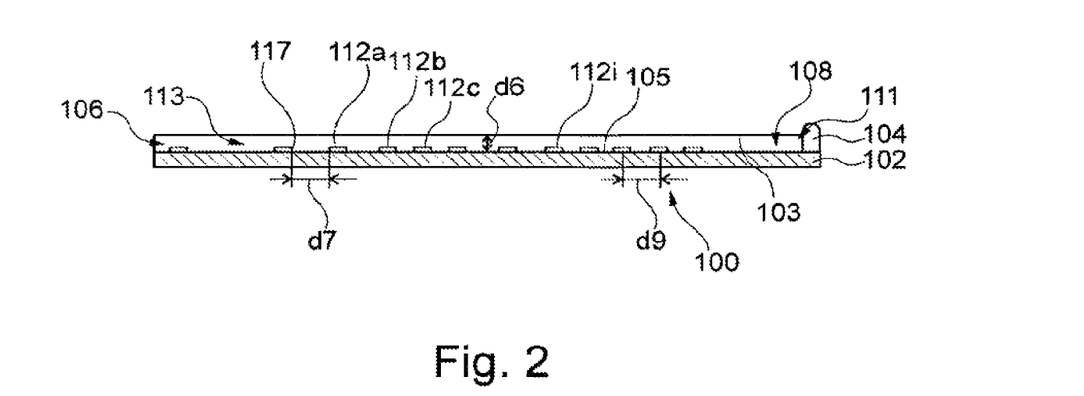
FIG. 2 is a side view of the microfluidic device of FIG. 1.

Referring to FIGS. 1 and 2, a microfluidic device 100 can be used to assay a sample to determine the presence (e.g., qualitatively and/or quantitatively) of multiple analytes. Microfluidic device 100 includes first and second substrates 102, 104 defining a micro fluidic network 107 including an inlet 106 and, in communication therewith, a channel 110 and a reservoir 108. Multiple spaced apart test zones 112$i$ are disposed within channel 110. Each test zone 112$i$ includes one or more reagents (e.g., probe compounds) configured to participate in an assay for an analyte. Channel 110 also includes a reference zone 117. Device 100 also includes a reference pattern 114 including multiple indicia 116$j$. Reference pattern 114 provides information related to spatial properties of test zones 112$i$.

Figure 4:
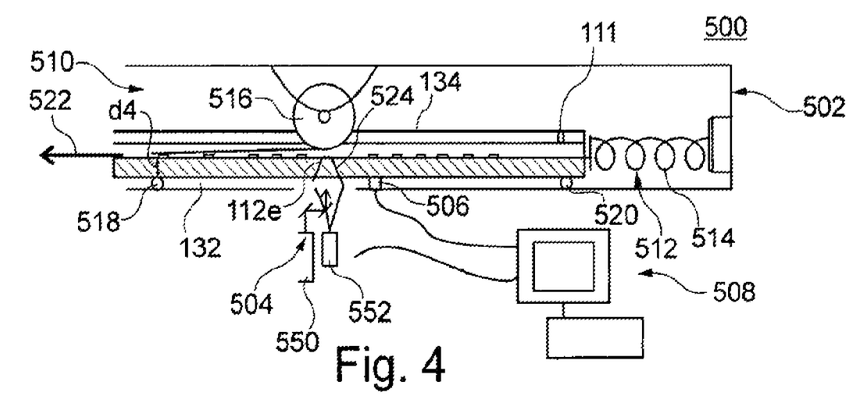

Referring to FIG. 4, operating system 500 includes a housing 502, a detector 504, a reference pattern reader 506, and a processor in communication with detector 504 and pattern reader 508. Detector 504 is an optical fluorescence detector that detects interaction between a sample and test zones 112$i$. Detector 504 includes a light source 550 (e.g., a light emitting diode or a laser diode) and a zero$^{th}$ order light sensitive detector 552 (e.g., a photomultiplier tube or a photodiode, such as an avalanche photodiode). Reference pattern reader 506 reads reference pattern 114 of device 100 during operation of system 500.

We now discuss microfluidic device 100 and system 500 in greater detail.

First substrate 102 is typically optically transmissive (e.g., clear) with respect to a wavelength of light useful for exciting and detecting fluorescence from fluorescent labels. For example, first substrate 102 may transmit at least about 75% (e.g., at least about 85%, at least about 90%) of incident light in at least one wavelength range between about 350 nm and about 800 nm. First substrate 102 can be formed of, for example, a polymer, glass, or silica. Second substrate 104 is typically formed of a pliable or flexible material (e.g., an elastomeric polymer). First substrate 102 may be less flexible than second substrate 104. For example, first substrate 102 may be substantially rigid (e.g., sufficiently rigid to facilitate handling of device 100).

Channel 110 is a capillary channel. A sample 113 applied to inlet 106 migrates along channel 110 by capillary force. Channel 110 is oriented along a major axis a1. Reservoir 108 includes a vent 111 to prevent gas buildup ahead of the sample. Each test zone 112$i$ typically includes a reagent (e.g., a probe compound) configured to provide a detectable interaction in the presence of an analyte. The interaction can include, for example, binding of a corresponding analyte to a probe compound of the test site and/or a chemical reaction between the corresponding analyte and the probe compound. The reaction results in a detectable product (e.g., a precipitate, a fluorescent material, or other detectable product). Exemplary probe compounds include proteins, antibodies, and polynucleotides. Suitable probe compounds for determining the presence of an analyte are described in Appendix A, U.S. provisional application 60/826,678 filed 22 Sep. 2006.

Figure 3A:
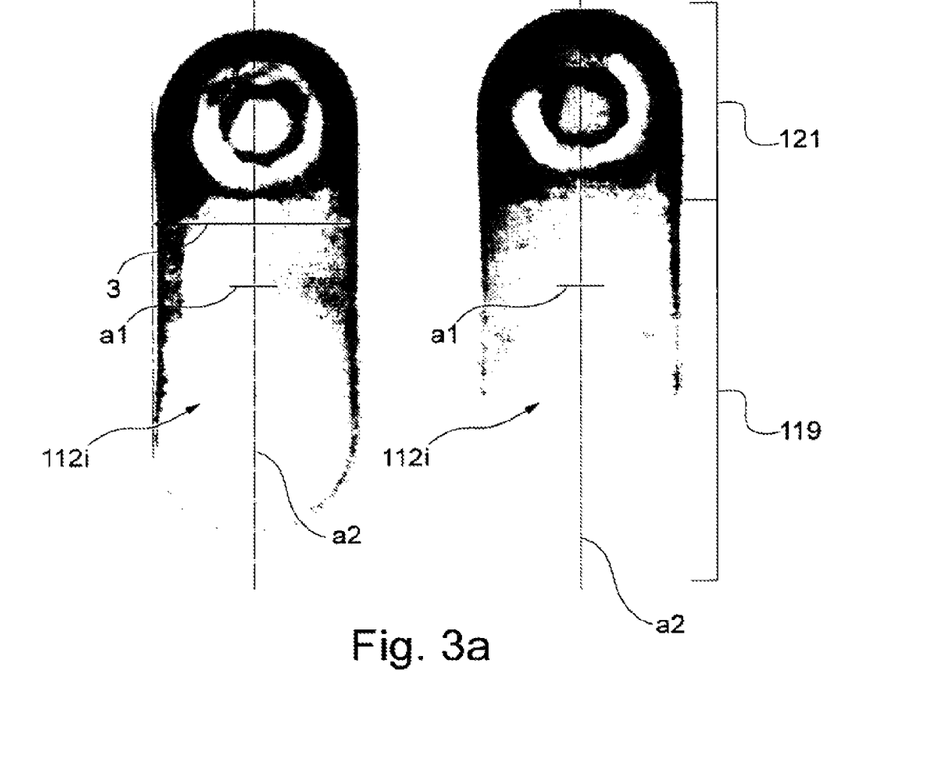
FIG. 3a shows top views of two test zones of the microfluidic device of FIG. 1.

Referring also to FIG. 3$a$, each test zone 112$i$ is elongate having a major axis a2 oriented generally perpendicular to major axis a1 of channel 110. Typically, a ratio of a length along major axis a2 to a width w along a perpendicular dimension of the test zones 112 is at least 2.5 (e.g., at least 5). The length along axis a2 is typically at least about 200 um (e.g., at least about 350 microns) and typically about 2000 um or less (e.g., about 1000 um or less, about 750 um or less). Width w is typically at least about 25 um (e.g., at least about 50 microns) and typically about 500 um or less (e.g., about 250 um or less, about 150 um or less). In an exemplary embodiment, test zones 112 are about 500 um long and about 100 um wide.

As seen in FIG. 2, test zones 112$i$ are spaced apart from adjacent test zones by a distance d7 along channel 110. Distance d7 between test zones 112$i$ is discussed further below in relation to a detection zone of detector 504.

Test zones 112$i$ can be formed as desired. In general, the reagents are contacted with 20 the first substrate. Then, the reagents and substrate are relatively translated laterally to form an elongated test zone.

Figures 3B, 3C, 3D, 3E, 3F, 3G:
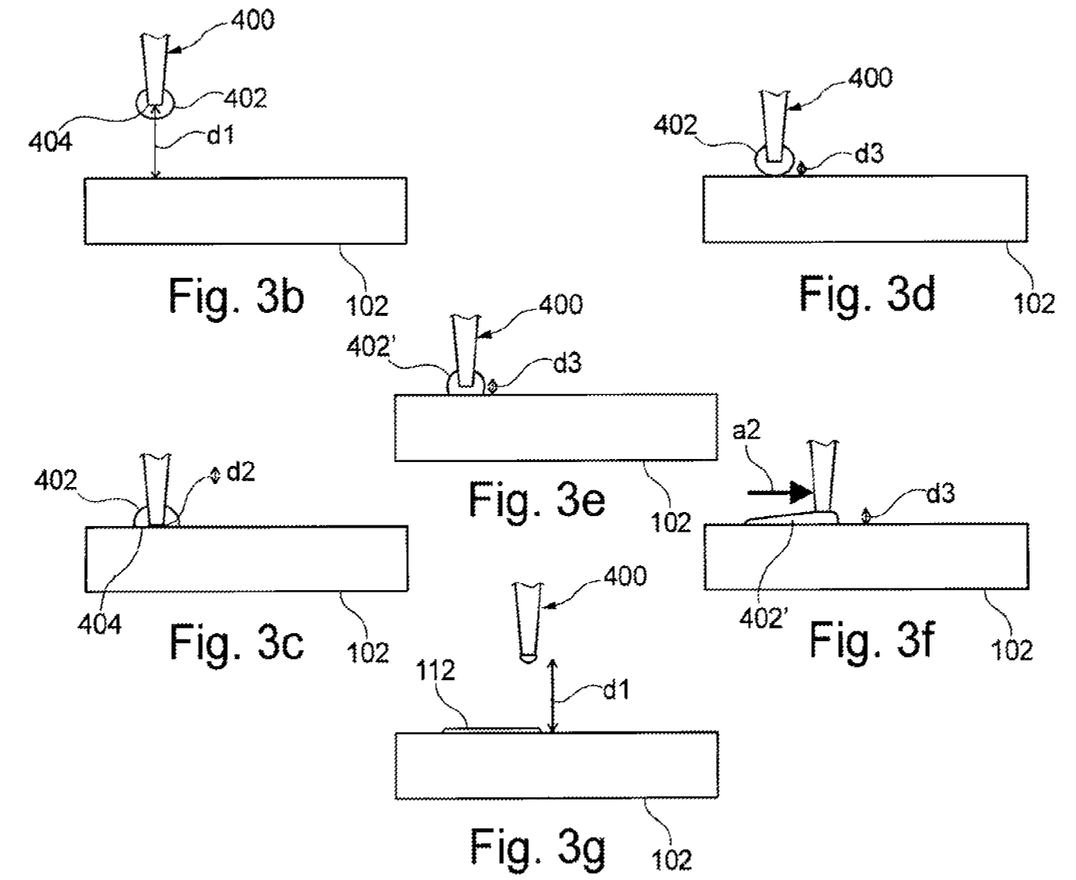

Referring to FIGS. 3$b$-3$g$, a method for forming test zones 112$i$ includes dispensing reagents from a capillary spotter 400 onto first substrate 102. In FIG. 3$b$, an amount (e.g., between about 2 and 8 nl, between about 3 and 5 nl) of reagent solution 402 containing one or more probe compounds is introduced to a distal tip 404 of a capillary of a capillary spotter. Distal tip 404 typically has a diameter of between about 80 and 120 um (e.g., about 100 um). Reagent solution 402 and substrate 102 are initially separated (e.g., not in contact) by a distance d1. Typically, d1 is at least about 250 um (e.g., about 500 um).

In FIG. 3$c$, tip 404 and substrate 102 are brought to a smaller separation d2 so that reagent solution 402 contacts a location of substrate 102. At the smaller separation d2, distal tip 404 is adjacent the location of substrate 102 (e.g., touching so that d2 is zero). Distal tip 404 and substrate 102 are maintained for a time (e.g., about 1 second or less, about 0.5 seconds or less, about 0.25 seconds or less) at separation d2 in the adjacent (e.g., touching) position. In some embodiments, the time for which distal tip 402 is maintained in the adjacent (e.g., touching) position is indistinguishable from zero.

In FIG. 3$d$, distal tip 404 and substrate 102 are moved to an intermediate separation d3 in which distal tip 404 and substrate remain connected by reagent solution 402 of distal tip 404. Typically, intermediate separation d3 is at least about 5 um (e.g., at least about 10 (j,m) and about 30 pm or less, about 25 um or less). In an exemplary embodiment, intermediate separation d3 is about 20 pm.

In FIG. 3$e$, distal tip 404 and substrate 102 are maintained at intermediate separation d3 for an incubation time so that at least some (e.g., at least about 10%, at least about 25%, at least about 40%) of reagent solution 402 at the distal tip evaporates so that only a remaining portion 402' of reagent solution 402 remains. Typically, only about 75% or less (e.g., about 50% or less) of reagent solution 402 evaporates to leave solution 402' remaining. The incubation time depends on the nature of the solution 402 (e.g., the probe compound concentration and the solvent vapor pressure) and distal tip 404 environment (e.g., the relative humidity and temperature). Typical incubation times are longer (e.g., at least 5 times as long, at least 10 times as long, at least 20 times as long, at least about 35 times as long) than the period of time for which the tip and substrate are in the adjacent position d2. Exemplary incubation times are at least about 5 seconds (e.g., at least about 10 seconds, at least about 20 seconds, at least about 25 seconds).

In FIG. 3f, after the incubation time at intermediate separation d3, at least one of the distal tip 404 and substrate 102 are moved laterally relative to the other to dispense reagent solution 402' along a major axis a2. In FIG. 3g, at the completion of the lateral movement, distal tip 402 and substrate 102 are separated so that they are no longer connected by the reagent solution. For example, distal tip 404 and substrate 102 can be returned to initial separation d1. The method can be repeated (e.g., using different reagent solution) to dispense elongate test zones at each of multiple locations of the substrate.

In general, the vertical separation of the distal tip and substrate is changed by moving the distal tip relative to the substrate. In general, the lateral translation of the distal tip and substrate is performed by translating the substrate relative to the distal tip. Exemplary reagent solutions, probe compounds, and dispensing devices are described in Appendix A, U.S. provisional application 60/826,678 filed 22 Sep. 2006.

Figure 8A:
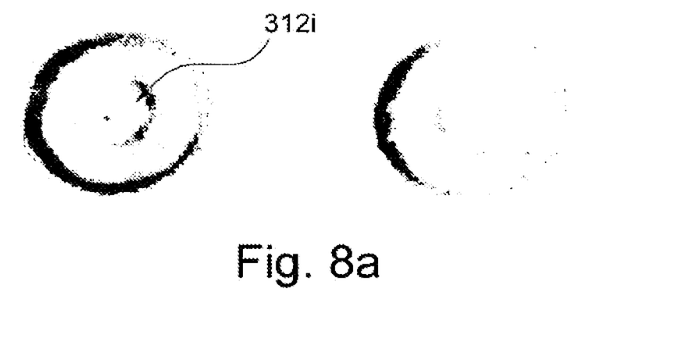
FIGS. 8a and 8b are each top views of two test zones of the microfluidic device of FIG. 7.
Figure 8B:
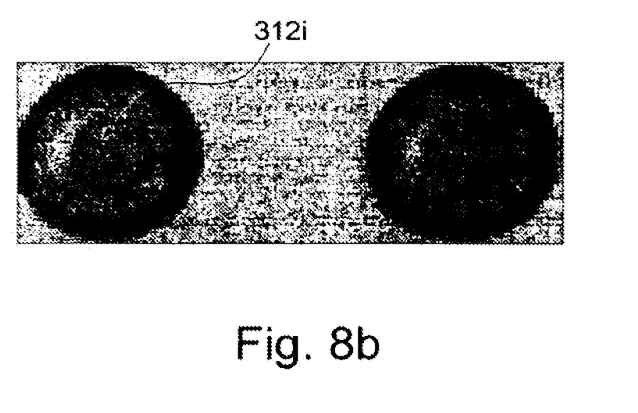

As seen in FIG. 3a and referring also to FIGS. 8a and 8b, the method for producing elongate test zones 112i provides a more homogenous distribution of probe compounds than a dispensing method that omits the step of lateral moving the distal tip and substrate. Test zones 112i include a first portion 119 and a second portion 121. The distribution of probe compounds in the first portion 119 is more homogenous than in second portion 121 or in test zones 312i, which were prepared without the step of lateral movement.

Returning to FIG. 1, reference zone 117 produces a response detectable by detector 504 independent of the presence of any analyte in a sample. Reference zone 117 typically includes a fluorescent medium (e.g., a polymer or immobilized fluorescent molecule). Reference zone 117 is discussed further below in regard to operation of system 500.

Indicia 116j of reference pattern 114 are configured to be read by reference pattern reader 506 of system 500. Indicia 116j are composed of magnetic material (e.g., magnetic ink). Pattern reader 506 can detect the presence of indicia 116j. Reference pattern 114 is discussed further below in regard to operation of system 500.

Returning to FIG. 4, housing 502 of operating system 500 includes an opening 510 to receive device 100, a compression system including a compression roller 516 and support rollers 518,520, and a translation actuator 512 including a damped spring 514. When device 100 is received within housing 500, detector 504 defines an optical detection zone 524 within channel 110. In use, device 100 is translated with respect to detection zone 524. Test zones 112i sequentially pass into and out of the detection zone. Detector 504 sequentially detects the interaction between a sample and successive test zones 112i. Detector 504 also senses reference zone 117.

Figure 6:
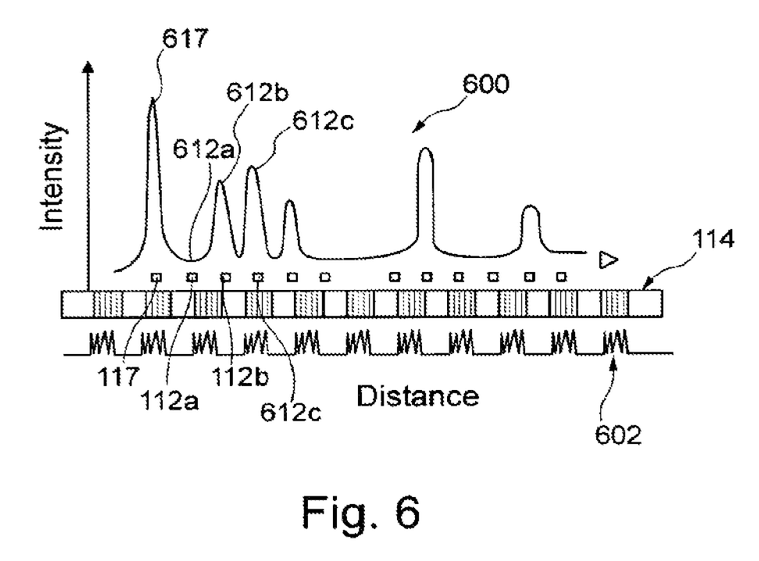
FIG. 6 illustrates fluorescence intensity data as a function of position along a channel of the microfluidic device of FIG. 1.

Referring to FIG. 6, detector 504 outputs a signal 600 as a function of the distance (relative or absolute) that device 100 is translated. Signal 600 includes a peak 617 indicative of reference zone 117 and peaks 612i indicative of the interaction at each zone 112i. Simultaneously, pattern reader 506 outputs a signal 602 indicative of indicia 116i as a function of distance that device 100 is translated. Because indicia 116i are related spatially to test zones 112i, processor 508 can determine when detection zone 524 coincides with a particular test zone even if that test zone exhibits no signal (e.g., as for test zone 112a which exhibits a signal 612a that is indistinguishable from zero). Reference zone 117 and corresponding signal 617 can be used alternatively or in combination with signal 602 to determine which regions of signal 600 correspond to particular test zones.

We next discuss the compression system. In use, the compression system compresses device 100 to reduce the distance between substrates 102,104 within channel 110. When device 100 is received within housing 502, an outer surface 132 of first substrate 102 is oriented toward support rollers 518,520 and an outer surface 134 of second substrate 104 is oriented toward compression roller 516. A distance d4 between support rollers 518,520 and compression roller 516 is less than a thickness t1 (FIG. 5) of device 100. Because second substrate 104 is relatively flexible as compared to first substrate 102, compression roller 516 compresses second substrate 104 causing a local reduction in distance d6 between inner surface 103 of second substrate 104 and inner surface 105 of first substrate 102.

In the relaxed state (e.g., uncompressed state) (FIG. 2), distance d6 is typically at least about 25 um (e.g., at least about 50 um, at least about 75 um). In the uncompressed state, distance d6 is typically about 500 um or less (e.g., about 250 um or less). In the locally reduced distance state (e.g., locally compressed state) (test zone 112e in FIG. 4), distance d6 is typically about 15 um or less (e.g., about 10 um or less, about 5 um or less, e.g., about 2.5 um or less). Examples of fluorescence detection performed between surfaces separated by a reduced distance state are described in U.S. continuation of International Patent Application PCT/EP2005/004923, Appendix B, U.S. application Ser. No. 11/593,021.

Figure 5:
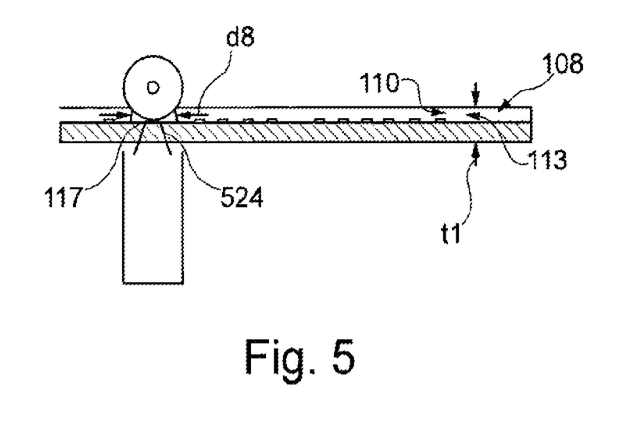

As seen in FIGS. 4 and 5, the compression system reduced distance d8 within channel 110 over only a portion of the length of channel 110. Typically, distance d8 is about 5 times the length or less (e.g., about 3 times the length or less, about 2 times the length or less, about the same as) than distance d7 separating test zones 112i.

Typically, distance d7 is large enough that optical detection zone 524 defined by detector 504 encompasses fewer than all (e.g., 5 or fewer, 3 or fewer, 2 or fewer) of 25 test zones 112i within channel 110. In an exemplary embodiment, d7 is large enough that a width of detection zone 524 along major axis a1 of channel 110 does not simultaneously contact more than 3 (e.g., not more than two, not more than one) test zone 112i. A width of detection zone 524 perpendicular to major axis a1 of channel 110 is typically about the same as or less (e.g., no more than 75% of, no more than 50% percent of, no more than 30% of) the length of test zones 112i along axis a2 thereof.

In use, sample liquid is applied to inlet 106. Capillary force draws the sample along channel 110 toward reservoir 108. The sample liquid contacts test zones 112i along channel 110. Analytes within the sample interact with probe compounds of the test zones. After a suitable incubation time, device 100 is inserted into housing 500 to compress spring 514 of translation actuator 512. During insertion of device 100, compression roller 516 and support rollers 520 are spaced apart so that device 100 is not compressed. Once device 100 is fully inserted, detection zone 524 is positioned approximately overlapping reference zone 117. Compression roller 516 locally compresses channel 110 (FIG. 5).

When the interactions between the analytes of the sample and the test zones 112i are ready to be determined (e.g., after an incubation period), translation actuator 512 translates device 100 with respect to detection zone 524 of detector 504 (FIG. 4). Test zones 112i pass sequentially through detection zone 524 and are illuminated with light from light source. Compression roller 516 is arranged so that the localized reduction of distance d6 corresponds spatially to detection zone 524. Accordingly, light detector sequentially detects light from test zones 112i while each is in the locally reduced distance state (e.g., locally compressed state) (test zone 112e in FIG. 4). Fluorescence arising from each test zone is collected by lens and detected by light detector. The sequential localized reduction of distance d6 and optical determination continues until each test zone has translated through detection zone 524.

In addition to the probe compounds of each test zone and analytes, other materials are present in channel 110 between inner surface 103 of second substrate 104 and inner surface 105 of first substrate 102. Examples of such materials include sample concomitants and reagents (e.g., unbound or un-reacted optical probes). These materials typically produce background emission (e.g., fluorescence or scattered light) that is not associated with the interaction of the sample with test zones 112*i*. The intensity of the background emission is generally proportional to the amount of such materials remaining between the inner surfaces at the location corresponding to detection zone 524. The intensity of the optical signal that is indicative of the interaction at each test zone, however, is spatially localized in the vicinity of that test zone. Light detector receives and detects both fluorescence indicative of the interaction and the background emission. However, because of the displacement of liquid from between inner surfaces in the locally reduced distance state (e.g., locally compressed state) (test zone 112*e* in FIG. 4) signal-to-noise of fluorescence indicative of the interaction relative to background fluorescence is higher than in the relaxed state (e.g., un-reduced distance or uncompressed state) (FIG. 2).

Methods and devices for performing assays have been described. Examples of other embodiments are discussed next.

While inlet 106 has been described as an unobstructed opening, other configurations are possible. For example, an inlet may be configured with a syringe fitting (e.g., a gas-tight fitting) to receive a syringe. Alternatively, an inlet may be configured as a gasket through which a sample may be introduced by a needle. As another alternative, the inlet may be fitted with a one-way valve that allows sample to be introduced but not to exit.

While a microfluidic device has been described that fills by capillary action, other embodiments can be used. For example, system 500 can be designed to reduce an internal volume of the microfluidic network prior to application of the sample to the inlet. When the sample is applied, the internal volume is increased thereby drawing the sample in. Such a volume decrease can be accomplished with, for example, compression roller 516. For example, microfluidic device may be received within housing 500 so that damped spring 514 of translation actuator 512 is in a compressed state. Compression roller 516 is positioned to compress device 100 at a location corresponding to reservoir 108. This compression reduces an internal volume of reservoir 108. The volume reduction is about as great as (e.g., at least about 25% greater than, at least 50% greater than) the volume of sample to be received within device 100. With reservoir 108 in the compressed state, a volume of sample is applied to inlet 106 of device 100. Compression roller 516 is retracted away from inlet 106 toward an opposite end 137 of device 100. As roller 516 moves away from reservoir 108, the reservoir decompresses thereby increasing the internal volume of the microfluidic network. The volume increase creates a vacuum that sucks the sample into the device.

While micro fluidic devices having an open capillary channel have been described, other embodiments can be used. For example, the channel may include a medium occupying at least some (e.g., most or all) of the cross section of the channel along at least a portion of its length. Typically, the medium is one which to multiple probe compounds can be immobilized to define respective spaced apart test zones (e.g., capture volumes), each having capture sites disposed in three dimensions. Pores or voids in the medium permit liquid to permeate along the channel (e.g., by capillary action). Liquid movement along the channel may be assisted by or induced by, for example, generating a vacuum within the channel as described above. Typically, probe compounds are immobilized with respect to the porous medium to define spaced-apart test zones along the channel. Interaction of analytes with probe compounds of the test zones can be determined sequentially as described for test zones 112*i* of device 100. Because each test zone is disposed in three dimensions, reducing the distance between the opposed inner surfaces of the channel decreases the capture volume occupied by the immobilized probe compounds of the test zone. Optical detection is performed with the test zone in the reduced volume (i.e., reduced distance) state.

Figure 7:
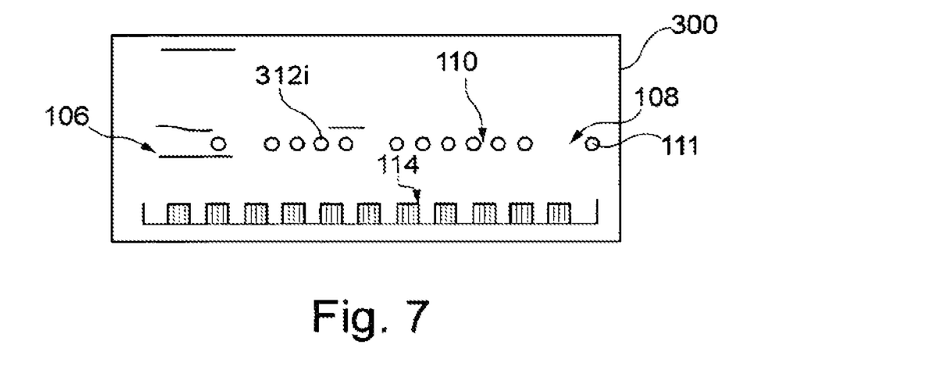
FIG. 7 is a microfluidic device.

While test zones 112*i* have been shown as elongate, other configurations are possible. For example, referring to FIG. 7, a microfluidic device 300 includes multiple test zones 312*i* each having a generally circular configuration. Other than a difference in shape, test zones 312*i* may be identical to test zones 112*i* of device 100. Other than a difference in test zones, devices 100 and 300 can be identical.

While a method for forming test zones 112*i* has been described as moving distal tip 404 and substrate 102 from an initial separation d1 (FIG. 3*b*) to an adjacent separation d2 (FIG. 3*c*) and to an intermediate separation d3 (FIG. 3*d*) prior to initiating lateral movement of distal tip 404 and substrate 102 (FIG. 3*f*), other embodiments can be performed. For example, distal tip 404 and substrate 102 can be moved laterally with tip 404 and substrate 102 in the adjacent separation d2. In this embodiment, separation d2 is typically greater than zero.

While a method for forming test zones 112*i* has been described as including a step of maintaining distal tip 404 and substrate 102 at an intermediate separation d3 for an incubation time until only a remaining portion 402' of reagent solution 402 remains, other embodiments can be performed. For example, lateral movement of distal tip 404 and substrate 102 can begin immediately as distal tip 404 and substrate 102 are moved from adjacent separation d2 (FIG. 3*c*) to separation d3 (FIG. 3*d*). In other words, the incubation time may be indistinguishable from zero. As another example, during the incubation, evaporating reagent solution may be replaced with additional reagent solution introduced to the capillary tip. Accordingly, the total amount of reagent at the capillary tip increases during the incubation.

While a method for forming test zones 112*i* has been described as including an incubation time with distal tip 404 and substrate 102 maintained at a separation d3, other embodiments can be performed. For example, separation d3 can vary during the incubation time. For example, tip 404 can be oscillated laterally and/or vertically relative to substrate 102 during the incubation time. Alternatively or in combination, tip 404 can be oscillated laterally and/or vertically relative to substrate 102 during lateral movement. Such oscillation can enhance transport of probe molecules to the first substrate during incubation or lateral motion.

While a method for forming test zones 112*i* has been described as using a capillary dispenser, other dispensers may be used. For example, material may be dispensed from a solid dispenser (e.g., a solid rod).

While a method for forming test zones 112*i* has been described as introducing an amount of reagent solution to a distal tip of a capillary of a capillary spotter (FIG. 3*b*) and bringing the tip and a substrate to a smaller separation d2 so that reagent solution 402 contacts a location of substrate 102, other embodiments can be performed. For example, reagent solution may be introduced to the distal tip only after the distal tip and substrate are brought to a smaller separation (e.g., after the distal tip is contacted with the substrate).

While a method and microfluidic device reader for sequentially reducing a distance between inner surfaces of a channel having been described, other configurations are possible. For example, a microfluidic device reader may be configured to simultaneously reduce a distance between inner surfaces along most (e.g., substantially all or all) of a channel. Subsequently, the reader translates the detection zone of a detector along the channel so that different test zones are read sequentially.

While a microfluidic device having a first relative rigid substrate and a second relatively flexible substrate has been described, other embodiments can be used. For example, the substrates define both opposed inner surfaces of a channel can be flexible. In such embodiments, a portion of the optical detector can form part of the compression system. For example, the microfluidic device may translate between a compression roller and an optic of the detector.

While a reference pattern has been described as providing information related to spatial properties of test zones of a microfluidic device, the reference pattern may provide additional or alternative information. For example, a reference pattern can provide information related to physiochemical properties of test zones of a 5 microfluidic device. Such properties include analytes for which the test zones are configured to assay. Other properties include the identity and properties of reagents stored on the device and date information (e.g., the expiration date) of the device.

While a reference pattern including magnetic indicia has been described, other indicia can be used. For example, the indicia may be formed of regions having different optical density or reflectance as compared to the surrounding material. The reference pattern reader is an optical reader typically configured to read the indicia by transmittance or reflectance.

The invention claimed is:

1. A system, comprising:
   a microfluidic device reader configured to receive a microfluidic device comprising an array of spaced-apart test zones, the test zones being disposed between an inner surface of a first substrate and an inner surface of a second substrate of the microfluidic device, at least one of the substrates being flexible, each test zone comprising a probe compound configured to participate in an assay for a target analyte,
   an optical detector includes a light source and is configured to sequentially detect light from at least one of the test zones when the at least one test zone is in a detection zone of the microfluidic device and the optical detector detects light when the distance between the inner surfaces at the corresponding location is reduced, wherein the detection zone has a width of detection perpendicular to major axis of channel,
   a translator configured to translate at least one of the microfluidic device and the detection zone of the optical detector relative to the other,
   a compressor configured to reduce a distance between the inner surfaces of the first and second substrates at locations corresponding to the detection zone of the optical device,
   a processor configured to receive a signal from the optical detector, the signal indicative of light detected from a test zone.

2. The system of claim 1, wherein the system is configured to simultaneously optically detect light from no more than a number N test zones, where $N \leq 5$.

3. The system of claim 2, where $N \leq 3$.

4. The system of claim 2, where $N = 1$.

5. The system of claim 1, wherein the detector is a fluorescence detector.

6. The system of claim 1, wherein the optical detector comprises a $zero^{th}$ order detector.

7. The system of claim 1, wherein the optical detector consists essentially of a $zero^{th}$ order detector.

8. The system of any of claim 1, wherein each test zone is elongate and defines a major axis and the translator configured to translate at least one of the microfluidic device translates the device along a translation axis generally perpendicular to the major axis of each of multiple test zones.

9. The system of claim 8, wherein the translation axis and the major axis of multiple of the test zones are perpendicular to within 10° or less.

10. The system of claim 9, wherein the translation axis and the major axis of multiple of the test zones are perpendicular to within 5° or less.

11. The system of claim 8, wherein the translation axis and the major axis of most of the test zones are generally perpendicular.

12. The system of claim 8, wherein the translation axis and the major axis of all of the test zones are generally perpendicular.

13. The system of claim 8, wherein a ratio of a length along the major axis to a width along a perpendicular dimension of the test zones is at least 2.5.

14. The system of claim 13, wherein the ratio is at least 5.

* * * * *